United States Patent [19]

Okada

[11] Patent Number: 4,752,286

[45] Date of Patent: Jun. 21, 1988

[54] BALLOON TUBE FOR TREATING ESOPHAGUS VARIX

[75] Inventor: Yosuke Okada, Tokyo, Japan

[73] Assignee: Sherwood Medical Company, St. Louis, Mo.

[21] Appl. No.: 809,533

[22] Filed: Dec. 16, 1985

[30] Foreign Application Priority Data

Dec. 19, 1984 [JP] Japan ............................ 59-192687[U]

[51] Int. Cl.$^4$ ............................................ A61M 25/00
[52] U.S. Cl. ..................................... 604/96; 604/102; 604/109; 604/101; 128/1 R
[58] Field of Search ................. 604/96, 101, 102, 104; 128/1 R

[56] References Cited

U.S. PATENT DOCUMENTS

| | | | |
|---|---|---|---|
| 2,854,982 | 10/1958 | Pagano | 604/101 |
| 4,180,076 | 12/1979 | Betancourt | 604/102 |

FOREIGN PATENT DOCUMENTS 683756  9/1979  U.S.S.R. ............................ 604/101

Primary Examiner—C. Fred Rosenbaum
Assistant Examiner—Sherri E. Vinyard

Attorney, Agent, or Firm—Stanley N. Garber; Andrew J. Beck; William R. O'Meara

[57] ABSTRACT

This invention provides an improvement in a method of surgically treating an esophageal varix utilizing an endoscope wherein air under pressure is directed to expand a patient's esophagus and wherein the varix is located, punctured and injected with a sclerosing material. The subject improvement involves directing a dual-lumen balloon tube through the patient's esophagus, the dual-lumen balloon tube including a primary suction lumen and a secondary inflation lumen. After the vatix is located, punctured and injected with sclerosing material, the balloon tube is partially withdrawn to position the balloon adjacent the varix and fluid under pressure is directed through the secondary lumen to inflate the balloon to thereby compress the varix to assist in stemming the flow of blood therefrom. Suction is then applied to the primary lumen to relieve pressure in the patient's stomach. This invention also provides an improved dual-lumen suction tube wherein the tube has a first portion constructed of a flexible but relatively hard plastic, and a second portion defining a distal end tube tip which is constructed of a relatively softer plastic than the first portion, such tube tip being mounted on a distal end of the first portion.

3 Claims, 3 Drawing Sheets

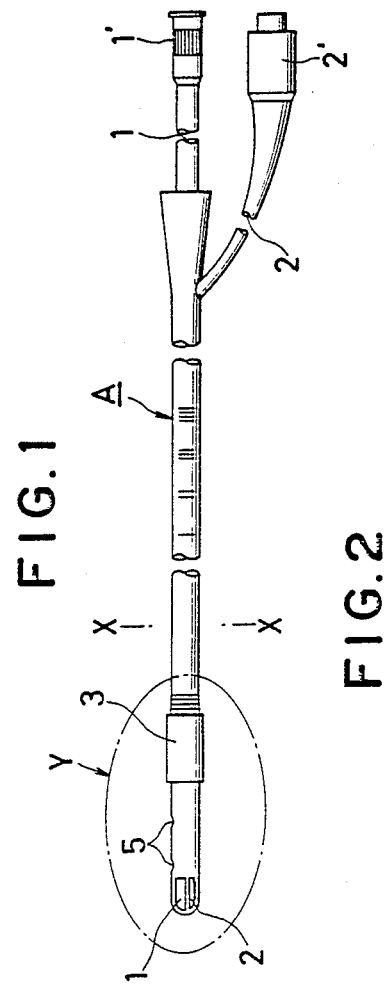
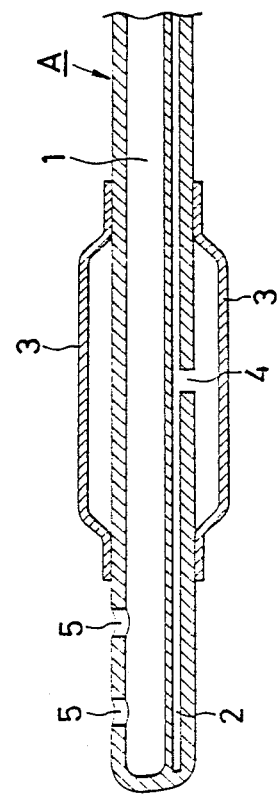
FIG. 1
FIG. 2
FIG. 3

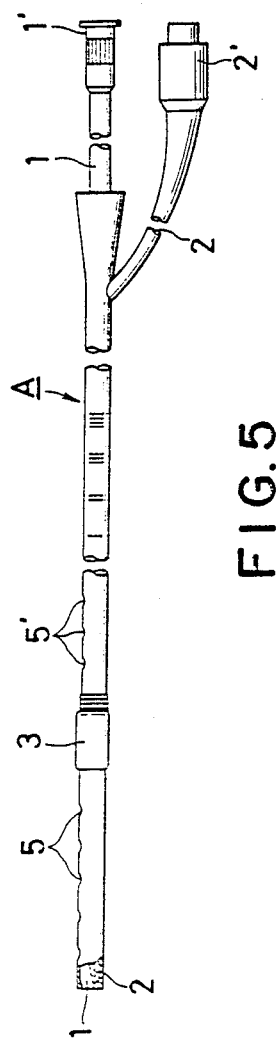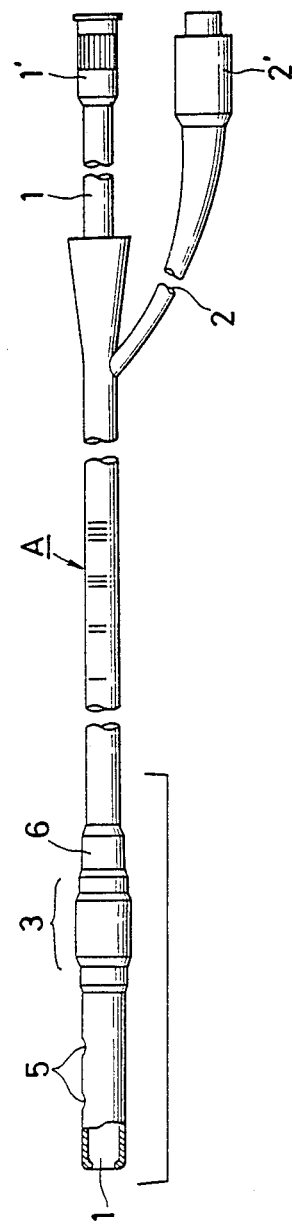

BALLOON TUBE FOR TREATING ESOPHAGUS VARIX

BACKGROUND OF THE INVENTION

1. Field of the Invention

The present invention relates to a method and apparatus for utilizing a balloon tube for treating esophagus varix. An esophagus or esophageal varix is a medical condition wherein certain of the esophageal veins of a patient become dilated or enlarged like varicose veins.

2. Description of the Prior Art

Recently, a medical treatment of esophageal varices has come in use wherein an endoscope is utilized to facilitate puncturing a varix after which an embolus or clot-forming material, such as a sclerosing fluid, is injected into the punctured varix to stem the flow of blood therefrom. According to this operation, a balloon tube is positioned in the stomach in advance and, after completion of the operation, the tube is pulled up to press the punctured vein.

In the past, this balloon tube so far used is in the form of a single tube merely provided at the distal end thereof with a balloom.

However, according to the aforesaid prior operation, air is fed through the top of the endoscope to ascertain the position of the varix while spreading the esophagus, and the dilated vein is punctured and injected. Therefore, the stomach is inflated with air to cause a patient considerable pain, and in the worst case, the operation has to be made again.

OBJECTS OF THE INVENTION

It is therefore an object of the present invention to provide a method and apparatus for utilizing a balloon tube for treatingan esophagus varix which can prevent the aforesaid stomach inflation and avoids injury of the interior of stomach caused by the distal end of the tube. It is a further object of the invention to provide a balloon for treating esophagus varix which can be used when severe bleeding occurs during the operation and the bleeding has to be immediately checked positively with the balloon.

It is another object of the invention to prevent the inflation of the stomach resulting from air fed from the endoscope by suction and reduction in pressure thereof through the tube.

SUMMARY OF THE INVENTION

The present invention may achieve the aforementioned objects by the provision of a balloon tube for treating an esophagus varix, the balloon tube comprising a double-lumen tube having a suction lumen in addition to a balloon inflating aeration lumen, the suction lumen having one or more small suction holes on one or both of the proximal and distal sides of the esophagus varix closing balloon. Preferably, the balloon tube has a diameter as small as possible so as not to impair the field of vision of the endoscope and so as not to disturb the puncturing operation. The balloon tube must have sufficient hardness since it is inserted into the stomach and actually, the tube used is a semihard tube having the size of 6 to 10 FR. (French) It might be expected therefore that the distal end of a small-diameter hard tube might easily damage the stomach wall. For this reason, a soft tube is arranged to encase the semi-hard tube only in the vicinity of the distal end of the semi-hard tube so as to minimize the damage in the stomach walls.

Further, to cope with re-bleeding during the operation, a stomach balloon is provided distally of the esophagus closing balloon in addition to the latter to provide for positive blood checking.

BRIEF DESCRIPTION OF THE DRAWINGS

FIG. 1 is an explanatory view of a balloon tube for treating esophagus varix in accordance with the present invention;

FIG. 2 is a sectional view taken on line X—X of FIG. 1;

FIG. 3 is an enlarged sectional view of Y-portion of FIG. 1;

FIG. 4 is an explanatory view of a further embodiment;

FIG. 5 is an explanatory view of another embodiment;

DETAILED DESCRIPTION OF THE INVENTION

Figure 6:
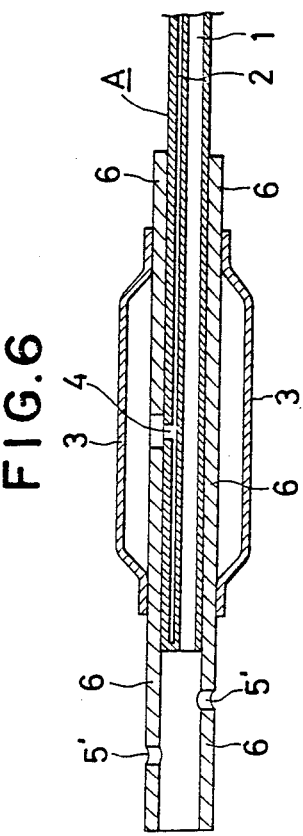
FIG. 6 is a sectional view in the neighbourhood of the balloon shown in FIG. 5.

In accordance with the present invention, the tube is of the double-walled lumen for balloon inflation and for suction, and small holes are provided near the distal end of the suction lumen, which holes are connected to a suction device so that pressure in the stomach may be reduced whenever necessary.

The present invention will be now described in detail by way of the embodiments shown in the drawings.

FIG. 1 is an explanatory view of a balloon tube for treating esophagus varix in accordance with the present invention. FIG. 2 is a sectional view taken on line X—X of FIG. 1. FIG. 3 is an enlarged sectional view of Y-portion in FIG. 1. Reference numeral 1 designates a main tube, and numeral 2 designates a balloon aeration lumen. The tube generally has a small diameter (outside diameter is approximately 2.7 to 4.0 mm) and is formed of somewhat hard plastic (principally formed of polyvinyl chloride, the amount of plasticizer is 30 to 40 PHR) (parts per hundred resin) having Shore hardness D of 50 to 60. A tube body indicated at A is provided within its inner wall with the balloon aearation lumen 2 over the full length thereof. A balloon 3 is mounted near the distal end of the tube A and is communicated with the aeration lumen 2 through the small hole 4, and air may be introduced therein to inflate the balloon 3. Small suction holes 5 may be provided to intake and remove blood and other body liquids in addition to air. FIG. 4 shows the case where small suction hole 5' for liquid are provided proximally of the balloon 3, whereby when saliva or the like stays frontwardly of the balloon during blood checking at the balloon, the saliva or the like may be collected and removed.

In FIG. 5, since the tube A is small in diameter and relatively hard, a soft tube 6 (principally formed of polyvinyl chloride, 60–90 PHR, Shore hardness A—6-0-80) is provided to encase the distal end of the tube A so as not to damage the inner walls of the esophagus by the distal end portion of the tube. A section of a portion near the balloon 3 is shown in FIG. 6. Thus, the balloon 3 increases in diameter, and internal pressure required to check bleeding will suffice. Small suction holes 5' are provided in the soft tube 6 forwardly of the balloon 3, and the soft tube 6 is also provided with small holes 4' in registration with the aeration small holes 4 in the tube so that aeration may be made into the balloon 3.

Figure 7:
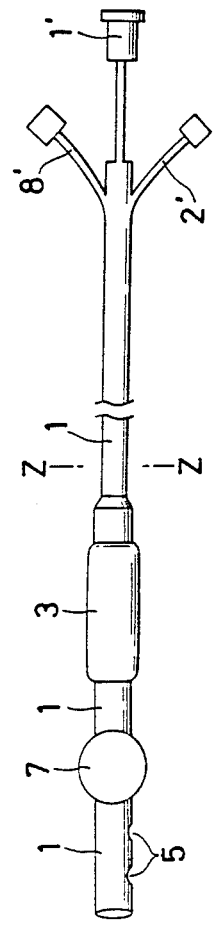
FIG. 7 is an explanatory view of a still another embodiment.
Figure 8:
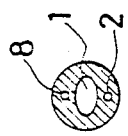
FIG. 8 is a sectional view taken on line Z—Z of FIG. 7.

In FIG. 7, a stomach balloon 7 is further provided forwardly of the esophagus balloon 3 of the balloon tube. The tube A used in this case is a tube having an aeration lumen 8 for the stomach balloon in the lumen wall as shown in FIG. 8 which shows it in section taken along the line Z—Z whereby aeration can be made into the stomach balloon through the aeration lumen 8. Reference numerals 2', 8' designate connections to aeration devices, and numeral 1' designates a connection to suction device.

With the above-described arrangement, according to the present invention, in the treatment of esophagus varix, not only the esophagus may be closed by the balloon but the discharge of air in stomach and drainage of blood or the like may be carried out whenever necessary. It will be noted that a tube whose distal end is formed of a soft material is used so as not to damage stomach walls or esophagus walls, and a stomach balloon may also be mounted.

What is claimed is:

1. In a method of surgically treating an esophageal varix utilizing an endoscope a distal end of which is positioned within a patient's esophagus to direct air under pressure to expand the patient's esophagus and wherein the varix is located, punctured and injected with a sclerosing material, the improvement comprising:

directing a relatively thin, dual-lumen suction tube through the patient's esophagus to position the distal end of the suction tube in the patient's stomach, the suction tube including a primary suction lumen for relieving pressure in the patient's stomach and a secondary inflation lumen for directing fluid under pressure to inflate a balloon fixed near the distal end of the suction tube;

expanding the patient's esophagus by directing air under pressure thereto; locating and puncturing the varix and injecting the sclerosing material into the varix;

at least partially withdrawing the endoscope and partially withdrawing the suction tube to position the balloon adjacent the varix;

directing fluid under pressure through the secondary lumen of the suction tube to inflate the balloon to thereby compress the varix and assist in stemming the flow of blood therefrom; and suctioning the patient's stomach utilizing the primary suction lumen of the suction tube in order to relieve pressure in the patient's stomach.

2. In the method of claim 1, wherein the suction tube further comprises suction holes in the primary suction lumen adjacent the balloon on the proximal side thereof, said improvement further comprising removing body fluids in the patient's esophagus above the balloon while compressing the varix and relieving pressure in the patient's stomach.

3. In the method of claim 2 wherein the suction tube further comprises a third lumen for directing fluid under pressure to inflate a second balloon on the distal side of the balloon adapted to be positioned adjacent the varix, the improvement further comprising directing fluid under pressure to the second balloon to inflate the same and block the stomach from communication with the esophagus while relieving pressure therin.

* * * * *